under 37 CFR 1.53(d), and is subject to the twenty year patent term provisions of 35 U.S.C. 154(a)(2).

US005994534A

United States Patent [19]

Capuder

[11] Patent Number: 5,994,534
[45] Date of Patent: *Nov. 30, 1999

[54] PROCESS FOR THE PREPARATION OF PHARMACEUTICALLY ACCEPTABLE SALTS OF CLAVULANIC ACID

[75] Inventor: Egidij Capuder, Krtina, Slovenia

[73] Assignee: Lek Pharmaceutical and Chemical Co. D.D, Ljubljana, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,172
[22] PCT Filed: Mar. 11, 1996
[86] PCT No.: PCT/GB96/00558
  § 371 Date: Nov. 24, 1997
  § 102(e) Date: Nov. 24, 1997
[87] PCT Pub. No.: WO96/28452
  PCT Pub. Date: Sep. 19, 1996

[30] Foreign Application Priority Data

Mar. 10, 1995 [SI] Slovenia ................. 9500074

[51] Int. Cl.$^6$ .................. C07D 503/00; C12P 17/18; C12N 1/02
[52] U.S. Cl. ..................................... 540/349
[58] Field of Search ............................ 540/349

[56] References Cited

U.S. PATENT DOCUMENTS

| | | | |
|---|---|---|---|
| 4,465,693 | 8/1984 | Strauss | 424/365 |
| 4,886,602 | 12/1989 | Kuehne et al. | 210/637 |
| 4,911,847 | 3/1990 | Shmidt | 210/650 |
| 5,073,263 | 12/1991 | Fagundas | 210/321.83 |
| 5,126,053 | 6/1992 | Schneider | 210/640 |
| 5,130,241 | 7/1992 | Woroniecki | 435/119 |
| 5,240,600 | 8/1993 | Wang | 210/188 |
| 5,470,356 | 11/1995 | Meszaros | 8/652 |
| 5,470,481 | 11/1995 | Modell | 210/652 |
| 5,650,101 | 7/1997 | Newkome | 264/4.3 |
| 5,691,141 | 11/1997 | Koster | 435/6 |
| 5,780,274 | 7/1998 | Capruder | 435/119 |
| 5,837,365 | 11/1998 | Chung | 521/905 |
| 5,858,892 | 1/1999 | Kinoshita | 501/12 |

FOREIGN PATENT DOCUMENTS

| | | |
|---|---|---|
| 400846 | 3/1996 | Austria . |
| 0 312 813 | 4/1989 | European Pat. Off. . |
| 0385552 | 5/1990 | European Pat. Off. . |
| 0562583 | 9/1993 | European Pat. Off. . |
| 0748387 | 9/1995 | European Pat. Off. . |
| 04295494 | 4/1992 | Japan . |
| 1 508 977 | 4/1978 | United Kingdom . |
| 1 563 103 | 3/1980 | United Kingdom . |
| 95 23870 | 9/1995 | WIPO . |
| 95 34194 | 12/1995 | WIPO . |
| 97/05142 | 2/1997 | WIPO . |

OTHER PUBLICATIONS

Belter, Ed, "Bioseparations" (Wiley and Sons, NY), pp. 13–17, 39–42, 237–238, 250–255, 1988.
Kent, ed, "Riegel's Handbook of Industrial Chemistry, Ninth Edition" (Van Nostrand Reinhold, NY) pp. 935, 937, 973–974, 1992.
Derwent, Abstract No. 92–395374/48 of JP–04295494, (1992).
Belter, et al., "Downstream Processing for Biotechnology", *Bioseparations*, Ch. 2, pp. 13–42, Ch. 9, pp. 237–255 (1988).
Noble, Richard D., "Principles and Applications," *Membrane Separations Technology Series 2*, pp. 354–413, (1995).
Notice of Opposition to a European Patent, pp. 1–22, (Jul. 22, 1998).
Rompp Chemie Lexikon, 9$^{th}$ edition, vol. 4 (1991), p. 2779.
Rompp Chemie Lexikon, 9$^{th}$ edition, vol. 6 (1992), p. 4798.
Michaels, et al., "Membranes in Biotechnology: State of the Art," *Desalination*, vol. 53, pp. 231–258, (1985).
Derwent for JP4–75596 (1992).
Derwent for JP60–70092 (1985).
Schweitzer, Philip A., "Membrane Filtration Section 2.1", *Handbook of Separation Techniques for Chemical Engineers*, Second Edition, 1988, pp. 2–4 through 2–103.

*Primary Examiner*—Mark L. Berch
*Attorney, Agent, or Firm*—Beyer & Weaver, LLP

[57] ABSTRACT

Provided is a process for preparation of pharmaceutically acceptable metal salts of clavulanic acid which avoids the use of toxic amines or other intermediates. The process involves removing solids from a clavulanic acid containing fermentation broth by microfiltration; acidifying the microfiltrate to a pH of between 1 and 3; extracting the acidified microfiltrate with a water immiscible solvent and separating the clavulanic acid containing extract; without converting the clavulanic acid containing extract to an intermediate clavulanate salt, mixing the extract with a metal donor and at least one additional non-aqueous solvent; and separating a pharmaceutically acceptable metal clavulanate salt from the solution.

17 Claims, No Drawings

PROCESS FOR THE PREPARATION OF PHARMACEUTICALLY ACCEPTABLE SALTS OF CLAVULANIC ACID

BACKGROUND OF THE INVENTION

This invention relates to a process for preparation of pharmaceutically acceptable salts of clavulanic acid, particularly but not exclusively alkali salts especially potassium clavulanate.

Clavulanic acid is the common name for (2R,5R,Z)-30 (2-hydroxyethylidene)-7-oxo-4-oxa-1-azabicyclo[3.2.0] heptane-2-carboxylic acid. Clavulanic acid and its alkali metal salts and esters are active as inhibitors of beta lactamase produced by some Gram positive as well as Gram negative micro-organisms. In addition to inhibition of beta lactamase, clavulanic acid and alkali metal salts thereof also have a synergistic action with penicillin and cephalosporin antibiotics. Clavulanic acid and its salts are used in pharmaceutical preparations to prevent the deactivation of beta lactam antibiotics. Commercial preparations contain potassium clavulanate in combination with amoxycillin trihydrate. Potassium clavulanate is more stable than the free acid or other salts.

Clavulanic acid is prepared by fermentation of a micro-organism such as strains of Streptomyces such as S. clavuligerus NRRL 3585, S. jimonjinensis NRRL 5741 and S. katsurahamanus IFO 13716 and Streptomyces sp. P5621 FERM P2804. The aqueous culture obtained after fermentation is purified and concentrated in accordance with conventional processes for example filtration and chromatographic purification as disclosed in GB 1508977, prior to extraction of the aqueous solution with an organic solvent to obtain a solution of impure clavulanic acid in the solvent.

GB 1508977 discloses preparation of clavulanate salts by filtration of the fermentation broth by passage through an anionic exchange resin. This process may achieve acceptable yields but sophisticated chromatographic purification methods are required and the use of resin columns involves substantial investment for manufacture on a commercial scale.

GB 1543563 discloses a fermentation process wherein the pH value of the medium is maintained in the range 6.3 to 6.7. Pharmaceutically acceptable salts such as potassium clavulanate are prepared by re-salting from lithium clavulanate. GB 1563103 discloses a process wherein crude clavulanic acid is obtained by primary isolation processes with a subsequent purification process being necessary.

EP-A-0026044 discloses use of the tertiary butylanine salt of clavulanic acid as an intermediate for purification of clavulanic acid. This salt was known from BE-862211 or DE 2733230 which disclosed that the salt was even more stable than the sodium or potassium clavulanate salts. Tertiary butylamine is a toxic compound and is also difficult to remove from waste water giving rise to serious pollution concerns.

EP-A-0312813 discloses a process for purification of clavulanic acid via the intermediate lithium salt.

EP-A-0562583 discloses use of salts of clavulanic acid with N,N'-monosubstituted symmetric ethylene diamines such as N,N'-diisopropylethylene diammonium diclavulanate as useful intermediates for isolation and preparation of pure clavulanic acid or alkaline metal clavulanate salts from ethyl acstate extract.

WO93/25557 discloses use of clavulanate salts with numerous amines as intermediates for preparation of clavulanic acid or pharmaceutically acceptable salts or esters.

EP-A-0594099 discloses use of tertiary octylamine with clavulanic acid as an intermediate in preparation of clavulanic acid or pharmaceutically acceptable salts.

WO94/21647 discloses use of N,N'-substituted diamines such as N,N'-diisopropylethylene diammonium diclavulanate as a useful intermediate for preparation of clavulanic acid and alkali salts.

WO94/22873 discloses use of novel tertiary diammonium salts of clavulanic acid such as N,N,N',N'-tetramethyl-1,2-diaminoethane clavulanate as a useful intermediate for preparation of clavulanic acid and salts thereof.

The aim of this invention is to prepare clavulanic acid and its pharmaceutically acceptable salts, such as potassium clavulanate in a new and simple manner, wherein the desired substance is obtained in a high yield and of high purity, avoiding the use of toxic amines.

SUMMARY OF THE INVENTION

According to the present invention a process for preparation of a pharmaceutically acceptable salt of clavulanic acid comprises the steps of:

removing solids from a clavulanic acid containing fermentation broth by microfiltration;

acidifying the filtrate to a pH between 1 and 3;

extracting the acidified filtrate with a water immiscible solvent and separating the clavulanic acid containing extract;

mixing the extract with a metal donor and at least one additional non-aqueous solvent;

and separating the metal clavulanate salt from the solution.

DETAILED DESCRIPTION OF THE PREFERRED EMBODIMENTS

The clavulanic acid containing broth may be obtained by fermentation of a Streptomyces micro-organism such as Streptomyces sp. P6621 FERM P2804 as disclosed in JP Kokai 80-162993. Alternative Streptomyces strains may be employed.

Microfiltration of the broth may be carried out as disclosed in WO95/23870. In a preferred process according to this disclosure the aqueous fermentation broth containing crude clavulanic acid, mycelium, proteins and other suspended solid matter is purified by microfiltration at a pH value between 5.8 and 6.2 and a temperature about 20 to 40° C. The purified filtrate may be concentrated by reverse osmosis and then directly extracted in a series of counter-current centrifugal extractors with a water immiscible solvent, preferably ethyl acetate. The extraction is preferably carried out at a temperature between 15 to 25° C. and a pH between 1 and 3. The extract is then dried to a water content below 0.1 mol. %, further concentrated by evaporation and decolorised with active charcoal to obtain a completely dry organic phase.

In the conventional prior art process the organic phase has been reacted with an amine to form an intermediate which is isolated and subsequently converted to the desired clavulanate salt. The present applicant has surprisingly discovered that alkali clavulanate salts such as the potassium salt can he obtained in high purity by direct reaction of the dried extract with a metal donor in the presence of at least one additional solvent. The additional step of conversion to the alkyl ammonium clavulanate salt is avoided. It is believed that the process of the present invention is made available by the high purity of the filtrate following microfiltration and preferably ultrafiltration.

The metal donor may be an organic salt, carbonate, bicarbonate or hydroxide of potassium, sodium, lithium or magnesium. Use of an organic salt, preferably a carboxylic acid is preferred. Use of the potassium salt is preferred in view of the comparative stability of potassium clavulanate.

The carboxylic acid may be selected from acetate, propionate, hexanoate, benzoate and benzoate substituted with one or more $C_1$–$C_{10}$ alkyl groups, preferably $C_1$–$C_6$ alkyl groups; halogen; nitro; O, S or NR substituted heteroalkyl; $C_1$–$C_{10}$ alkyl substituted with a group: R, O R, S R, or N $R^1$ $R^2$ wherein R, $R^1$ and $R^2$ are independently $C_1$–$C_{10}$ alkyl Preferred metal donors include potassium 2-ethyl hexanoate, potassium acetate, lithium 2-ethyl hexanoate and lithium acetate.

The additional solvent may comprise a $C_1$–$C_{10}$ alcohol or mixtures thereof. Use of $C_1$–$C_4$ alcohols is preferred. Especially preferred additional solvents include methanol, ethanol, isopropanol and isobutanol and mixtures thereof. Use of isopropanol is especially preferred. These solvents are preferably dry, for example containing between 0% and 4% water.

The metal donor may be dissolved in the additional solvent prior to addition to the clavulanic extract. Alternatively the metal donor may be dissolved in the same solvent as the clavulanic acid extract, for example ethyl acetate and the additional solvent added separately.

Particularly advantageous results are obtained when potassium 2-ethyl hexanoate is dissolved in isopropanol, potassium acetate is dissolved in methanol or potassium benzoate is dissolved in methanol. The concentration of the potassium 2-ethyl hexanoate in isopropanol may preferably be 0.1 mol/l to 5 mol/l more advantageously 1 mol/l to 2.5 mol/l and preferably from 1.5 mol/l to 2 mol/l in a 0.8 to 5 molar excess based on the amount of clavulanic acid, preferably in a 5 to 25% molar excess.

The water immiscible solvent used to extract the filtrate of the fermentation broth is preferably selected from ethyl acetate, methyl acetate, propyl acetate, n-butyl acetate, ketones such as methyl ethyl ketone, alcohols such as n-butanol, n-amyl alcohol or halogenated solvents such as methylene chloride chloroform or ethers such as diethyl ether or hexane or mixtures thereof. Use of ethyl acetate as preferred. The extract may be purified with activated charcoal and if necessary a silica gel column.

The concentration of crude clavulanic acid in the dried concentrated extract of the water immiscible solvent such as ethyl acetate may be between 8 g/l and 40 g/l preferably between 20 g/l and 40 g/l.

The clavulanate extract, preferably in ethyl acetate, may be decolorised by addition of activated charcoal. An amount of 0.2 to 0.5 g of activated charcoal per gram of clavulanic acid has been found to be convenient although alternative amounts may be employed as desired.

According to a preferred embodiment of the present invention the fermentation broth is purified by successive microfiltration and ultrafiltration. Use of ultrafiltration affords an unexpectedly pure product which does not require a subsequent purification step involving isolation of an intermediate.

The ultrafiltration is preferably carried out using a polymeric membrane having a resolution of 10,000 to 30,000 Daltons, preferably 20,000 Daltons. The membrane may have a pore size of 1 to 100 nm. Continuous ultrafiltration is preferred so that the dwell times are as short as possible. Serially interconnected ultrafiltration devices are preferred.

The invention is further described by means of examples but not in any limitative sense.

EXAMPLE 1

A clavulanic acid containing Streptomyces fermentation broth was microfiltered, ultrafiltered, preconcentrated to pH 1.2 to 2.0 and extracted with ethyl acetate as disclosed in Example 1 of WO95/23870. The ethyl acetate extracts were concentrated on a distillation apparatus which most of the water was eliminated by azeotropic distillation. The resultant ethyl acetate solution of clavulanic acid solution (0.3 l, clavulanic acid content 25.4 g/l, water content 0.6 g/l) was treated with charcoal (1.75 g) and after removal of the charcoal by filtration potassium 2-ethyl hexanoate (2 M solution in isopropanol, 23.0 $cm^3$, 20% excess) was added dropwise over a period of 10 minutes. The mixture was cooled to 0 to 5° C. with stirring and the precipitated product was filtered after 1 hour. The product was dried under reduced pressure at 35° C. to yield potassium clavulanate (6.13 g, yield 55%, assay 68.1%).

EXAMPLE 2

An ethyl acetate extract of clavulanic acid (1 l clavulanic acid content 23.6 g/l) was stirred with charcoal (5.7 g) for 20 min. The mixture was filtered and the charcoal washed with isopropanol (0.33 l). The collected ethyl acetate/isopropanol solution was treated by dropwise addition of potassium 2-ethyl hexanoate (2 M solution in isopropanol, 71.5 $cm^3$, 20% excess) Procedure of Example 1 was followed and crystalline potassium clavulanate (20.14 g, yield 68%, assay 79.6%, USP grade) was isolated.

EXAMPLE 3

The ethyl acetate solution of Example 1 was treated according to the same procedure except that isopropanol was replaced with methanol (0.33 l). The yield of potassium clavulanate was 17.7 g (55%, assay 73.8%).

EXAMPLE 4

The procedure of Example 2 was repeated using absolute ethanol (0.33 l) instead of isopropanol to yield potassium clavulanate (9.3 g, yield 29%, assay 74.0%).

EXAMPLE 5

The procedure of Example 2 was repeated using isobutanol (0.33 l) instead of isopropanol to yield potassium clavulanate (19.8 g, yield 62%, assay 74.0%).

EXAMPLE 6

An ethyl acetate solution of clavulanic acid (26.7 g/l, 0.6 l) was treated with charcoal (3.6 g) and the filtrate was diluted with isopropanol (0.1 l) and acetone (0.1 l). Potassium 2-ethyl hexanoate (2 M solution in isopropanol, 48.5 $cm^3$, 20% excess) was added dropwise and the mixture was further treated as described in example 1 to yield potassium clavulanate (12.4 g, yield 60%, assay 77.0%).

EXAMPLE 7

Potassium 2-ethyl hexanoate (2 M solution in isopropanol, 8 $cm^3$ was added during vigorous stirring of clavulanic acid solution in ethyl acetate (1 l, assay 20.2 g/l)

and after 5 minutes charcoal, 4.5 g) was introduced into the mixture. After stirring for 20 minutes, solid particles were removed by filtration. Potassium-2-ethyl hexanoate (2M solution, 43 cm³ in isopropanol) was added in portions of 5 cm³ each minute). The mixture was then stirred below 0° C. for 30 minutes and the precipitated product was collected by suction, washed with acetone and dried as described in Example 1 to give potassium clavulanate (yield 58.7%, assay 80.1%, USP grade).

EXAMPLE 8

An aqueous solution of clavulanic acid obtained from fermentation Streptomyces was filtered, treated by ultrafiltration, preconcentrated, acidified with conc sulphuric acid to pH 1.5 to 2.0 and extracted with ethyl acetate in a continuous extraction process. The ethyl acetate extracts were concentrated on a distillation apparatus to remove most of the water by azeotropic distillation. The resultant solution (1 l, clavulanic acid 28.3 g/l, water content 0.5 g/l) was passed through a short column (height 20 cm, diameter 9 cm) containing silica gel (E Merck, Kiesel gel 60, 70 to 230 mesh, 440 g) and eluted with a flow of fresh ethyl acetate. The outcoming solution was collected in 250 cm³ portions. Clavulanic acid rich portions (7th to 12th portions, 1.25 l) were collected, treated with charcoal and diluted with isopropanol (300 cm³). After dropwise addition of potassium 2-ethyl hexanoate (2 M solution in isopropanol, 78.8 cm³, 10% excess) the mixture was stirred at 0° C. to 10° C. for 30 minutes and the precipitate was filtered, washed and dried to give potassium clavulanate (21.4 g, yield 61%, assay 81.2%, USP grade).

EXAMPLE 9

An ethyl acetate extract of clavulanic acid obtained in accordance with Example 1 was concentrated and dried over anhydrous magnesium sulphate to give a solution with clavulanic acid assay 16.6 g/l and a water content 5 g/l. 0.3 l of this solution was passed through a column of silica gel (diameter 5 cm, height 10 cm, 120 g). The clavulanic acid was eluted using ethyl acetate then after 600 cm³ of outflow this solvent was replaced with ethyl acetate/isopropanol 3:1 v/v mixture. The fractions which contain more than 0.5 g of clavulanic acid per liter were collected and treated with charcoal (0.5 g). A solution of potassium 2-ethyl hexanoate (2 M solution in isopropanol, 13.8 cm³, 10% excess) was added in a single portion and the mixture was stirred for 60 minutes. The resultant crystals were collected by filtration, washed and dried to give potassium clavulanate (3.97 g, yield 63.0%, assay 79.0% USP grade.

EXAMPLE 10

An aqueous solution of clavulanic acid obtained from a fermentation broth in accordance with Example 1 was acidified and then quickly extracted with isobutyl methyl ketone. The extract was dried with a magnesium sulphate, concentrated by evaporation and treated with charcoal. After filtration of the absorbent, potassium 2-ethyl hexancoate (2 M solution in isopropanol, 29.3 cm³, 15% excess) was added to the filtrate (1 l, clavulanic acid content 10.1 g/l) and the mixture was stirred at 0 to 5° C. for 60 min. Yellow crystals of potassium clavulanate were filtered, washed and dried to give 5.0 g (yield 29%, assay 59%).

EXAMPLE 11

A solution of clavulanic acid in ethyl acetate (0.3 l clavulanic acid content 22.6 g/l) was treated with charcoal and after removal of the charcoal by filtration, potassium acetate (1 M solution in methanol, 51 cm³, 50% excess) was added dropwise over a period of 15 minutes. The mixture was stirred for 30 min at 0 to 10° C. The precipitate was filtered, washed and dried to give potassium clavulanate (2.33 g, yield 25%, assay 72.3%).

EXAMPLE 12

An ethyl acetate extract of clavulanic acid (0.3 l, clavulanic acid content 22.9 g/l) was treated with charcoal as described in Example 1. A solution of lithium-2-ethyl hexanoate (1 M solution in methanol, 38.5 cm³, 10% excess) was added dropwise over a period of 10 minutes. The mixture was stirred at 0 to 10° C. for 30 minutes. The precipitate was filtered, washed and dried to give lithium clavulanate (4.85 g, 91.1%, assay 64%).

EXAMPLE 13

A cry concentrated extract of crude clavulanic acid in ethyl acetate prepared in accordance with Example 1 having a clavulanic acid content of 32 g/l and water content below 2 g/l was decolorised by treatment with activated charcoal and dry methanol (80 cm³) was added. Potassium 2-ethyl hexanoate (2 M solution in isopropanol, 47 cm³) was added with vigorous stirring during 15 minutes at 20° C. The resultant suspension was cooled to 10° C. and the precipitate separated by filtration. The precipitate was washed with 2×50 cm³ portions of ethyl acetate and dried for 1 hour under vacuum at 40° C. Potassium clavulanate (10.4 g, assay 82.2%, USP grade) was obtained.

What is claimed is:

1. A process for the preparation of a pharmaceutically acceptable metal salt of clavulanic acid comprising the steps of:

removing solids from a clavulanic acid containing fermentation broth by successive microfiltration and ultrafiltration;

acidifying the microfiltrate to a pH of between 1 and 3;

extracting the acidified ultrafiltrate with a water immiscible solvent and separating the clavulanic acid containing extract;

without converting the clavulanic acid containing extract to an intermediate clavulanate salt, mixing the extract with a metal donor and at least one additional non-aqueous solvent;

and separating the pharmaceutically acceptable metal clavulanate salt from the solution.

2. A process as claimed in claim 1, wherein said clavulanate salt is USP grade potassium clavulanate.

3. A process as claimed in claim 1, wherein the ultrafiltration is continuous ultrafiltration.

4. A process as claimed in claim 1, wherein the metal donor is an organic salt, carbonate, bicarbonate or hydroxide of: potassium, sodium, lithium, calcium or magnesium.

5. A process as claimed in claim 4, wherein the metal is potassium.

6. A process as claimed in claim 4, wherein the metal donor is a carboxylic acid salt.

7. A process as claimed in claim 6 wherein the carboxylic acid is selected from: acetate, propionate, hexanoates, benzoates and benzoates substituted with one or more $C_1$–$C_{10}$ alkyl groups.

8. A process as claimed in claim 6, wherein the metal donor is selected from: potassium 2-ethyl hexanoate, potassium acetate, lithium 2-ethyl hexanoate and lithium acetate.

9. A process as claimed in claim 1, wherein the additional non-aqueous solvent is selected from: $C_1$–$C_{10}$ alcohols and mixtures thereof.

10. A process as claimed in claim 9, wherein the additional non-aqueous solvent is selected from $C_1$–$C_4$ alcohols and mixtures thereof.

11. A process as claimed in claim 1, wherein the additional non-aqueous solvent is selected from: isopropanol, methanol, ethanol, isobutanol and mixtures thereof.

12. A process as claimed in claim 1, wherein the water immiscible solvent is ethyl acetate or methyl isobutyl ketone.

13. A process as claimed in claim 10, wherein the water immiscible solvent is ethyl acetate and the ratio of ethyl acetate to the additional non-aqueous solvent is 3:1 to 10:1.

14. A process as claimed in claim 11, wherein the ratio is 5:1 to 7:1.

15. A process as claimed in claim 12, wherein the non-aqueous solvent is methanol.

16. A process as claimed in claim 1, wherein the extract is dried to a water content less than 6 g/l before addition of the metal donor.

17. A process as claimed in claim 1 to 16, wherein the broth is ultrafiltered using a membrane with pore sizes in the range of 1 to 100 nm.

* * * * *